(12) United States Patent
Nihei

(10) Patent No.: US 8,657,108 B2
(45) Date of Patent: Feb. 25, 2014

(54) PACKAGE CONTAINER FOR ORTHODONTIC MOUTHPIECE

(71) Applicant: GC Corporation, Bunkyo-ku (JP)

(72) Inventor: Kinya Nihei, Nerima-ku (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 13/743,501

(22) Filed: Jan. 17, 2013

(65) Prior Publication Data

US 2013/0180870 A1    Jul. 18, 2013

(30) Foreign Application Priority Data

Jan. 18, 2012   (JP) ................................. 2012-007648

(51) Int. Cl.
  *B65D 83/10*   (2006.01)
  *A61B 19/02*   (2006.01)

(52) U.S. Cl.
  USPC ........... 206/63.5; 206/368; 206/469; 206/470

(58) Field of Classification Search
  USPC ........ 206/63.5, 368, 369, 461, 467, 469, 470, 206/471, 459.5; 433/2, 6, 9, 24, 77
  See application file for complete search history.

(56) References Cited

U.S. PATENT DOCUMENTS

| | | | |
|---|---|---|---|
| 4,666,037 A * | 5/1987 | Weissman ..................... | 206/63.5 |
| 4,966,319 A | 10/1990 | Fleming | |
| 5,209,354 A | 5/1993 | Thornhill et al. | |
| 5,350,059 A * | 9/1994 | Chester et al. ............... | 206/63.5 |
| 5,429,229 A * | 7/1995 | Chester et al. ............... | 206/63.5 |
| 5,538,129 A * | 7/1996 | Chester et al. ............... | 206/63.5 |
| 6,082,995 A | 7/2000 | Wise | |
| 7,137,812 B2 * | 11/2006 | Cleary et al. .................. | 206/63.5 |
| 7,568,579 B2 * | 8/2009 | Moore .......................... | 206/368 |
| 7,910,632 B2 * | 3/2011 | Cinader et al. ............... | 206/63.5 |
| 2005/0074716 A1 | 4/2005 | Cleary et al. | |
| 2005/0133384 A1* | 6/2005 | Cinader et al. ............... | 206/63.5 |
| 2006/0207893 A1* | 9/2006 | Cinader et al. ............... | 206/63.5 |

FOREIGN PATENT DOCUMENTS

| | | |
|---|---|---|
| AU | 14512 76 A | 12/1977 |
| JP | 1134216 | 2/2002 |

OTHER PUBLICATIONS

Extended European Search Report issued Jul. 3, 2013 in Patent Application No. 13000221.5.

* cited by examiner

*Primary Examiner* — Luan K Bui

(74) *Attorney, Agent, or Firm* — Oblon, Spivak, McClelland, Maier & Neustadt, L.L.P.

(57) ABSTRACT

A packaging container is constructed by a packaging container main body with a lid portion, and a label adhered to an upper surface of the packaging container main body. An accommodating portion main body of the packaging container main body has a first flange portion around an accommodating portion, and second flange portions positioned at right and left side ends of the first flange portion and extending in an outward direction from an upper end of each of step portions having the same height as a thickness of the lid portion. Further, an engagement concave portion engaging with an engagement portion of the lid portion is formed in a front portion in the center of the first flange portion, and the label is adhered to upper surfaces of the lid portion and the second flange portions to seal the container main body, and is unsealed by a cut line.

2 Claims, 4 Drawing Sheets

PACKAGE CONTAINER FOR ORTHODONTIC MOUTHPIECE

BACKGROUND OF THE INVENTION

1. Field of the Invention

The present invention relates to a packaging container for an orthodontic mouthpiece, which is for packaging an orthodontic mouthpiece.

2. Description of the Conventional Art

In an orthodontic field, a medical treatment for correcting a teeth alignment and an occlusion has been conventionally carried out by installing a bracket to a front surface or a back surface of teeth, inserting and connecting an arch wire to a wire slot of the bracket, and utilizing an elastic restoring force of the arch wire.

In recent years, in addition to the orthodontic treatment using the bracket and the arch wire mentioned above, an orthodontic treatment using a detachable and transparent orthodontic mouthpiece has been going to be carried out. The orthodontic treatment is a method of correcting a teeth alignment and an occlusion little by little by newly preparing orthodontic mouthpieces having changed shapes in correspondence to a condition of an arrangement of the patient's teeth per a period from about two weeks to one month and sending them to the patient so as to replace, thereby utilizing the elastic restoring forces of the respective orthodontic mouthpieces. Since the transparent mouthpiece is installed without using any bracket and any wire, it is possible to treat in an inconspicuous manner. Further, since the mouthpieces can be easily attached and detached, there is an advantage that the mouthpieces can be detached at a time of taking a meal or cleaning the teeth. Therefore, the mouthpieces are frequently used for comparatively simple cases that it is unnecessary to extract a tooth.

The orthodontic mouthpiece used in the orthodontic treatment has been conventionally packaged, for example, by a packaging bag Y for the orthodontic mouthpiece, the packaging bag Y having a sealing portion Ya sealing the orthodontic mouthpiece and employing polyethylene as a raw material as illustrated in FIG. 6, or a packaging container Z for the orthodontic mouthpiece, the packaging container Z constituted by a plastic packaging container main body Za having an accommodating portion Zaa which accommodates the orthodontic mouthpiece and has a U-shaped transverse cross section, and a sealing seal Zb sealing an opening of the accommodating portion as illustrated in FIG. 7. However, in the case of packaging the orthodontic mouthpiece by the packaging bag Y for the orthodontic mouthpiece, a protection of the orthodontic mouthpiece is insufficient and there is a risk that the orthodontic mouthpiece is damaged at a time of carrying since the packaging bag is weak in a shock from an external portion. On the other hand, in the case of packaging the orthodontic mouthpiece by the orthodontic mouthpiece packaging container Z constituted by the plastic packaging container main body Za having the accommodating portion Zaa which accommodates the orthodontic mouthpiece and has the U-shaped transverse cross section, and the sealing seal Zb sealing the opening of the accommodating portion, the orthodontic mouthpiece can be accommodated in the accommodating portion Zaa of the plastic packaging container main body Za. Therefore, a risk that the orthodontic mouthpiece is damaged at a time of carrying is low. Further, it is possible to easily unseal by peeling the sealing seal Zb. However, since the sealing seal Zb can not seal again the opening of the accommodating portion of the packaging container main body Za once the sealing seal Zb is unsealed, it is burdensome to independently prepare a plastic storage container constituted by an accommodating portion main body for accommodating the orthodontic mouthpiece, a lid portion closing the accommodating portion main body, and a hinge portion bonding the accommodating portion main body and the lid portion, in preparation for the case of detaching the orthodontic mouthpiece, for example, during a meal or during a teeth cleaning work (for example, refer to patent document 1). Further, even in the case that such a storage container is prepared, it normally takes a long period of time over half year to carry out the orthodontic treatment using the orthodontic mouthpiece. Therefore, there has been a problem that contamination and bacteria are adhered to an inner portion of the storage container during a continuous use, and the inner portion of the container tends to come to an unsanitary state.

PRIOR ART DOCUMENT

Patent Document

Patent Document 1: Japanese Registered Design No. 1134216

SUMMARY OF THE INVENTION

Problem to be Solved by the Invention

In view of the above mentioned problems, an object of the present invention is to provide a packaging container for an orthodontic mouthpiece which can safely carry an orthodontic mouthpiece without damaging, can be easily unsealed, and can be used as a storage container after being unsealed.

Means for Solving the Problem

The earnest work was carried out by the inventor of the present invention, and as a result, a packaging container for an orthodontic mouthpiece is constructed by a packaging container main body made of plastic and constituted by an accommodating portion main body having an accommodating portion for accommodating an orthodontic mouthpiece and a hinge portion in a rear end of the accommodating portion main body and a lid portion so as to be freely opened and closed via the hinge portion, and a label made of paper, resin or cardboard being adhered to an upper surface of the packaging container main body so as to seal, and on which a product information of an orthodontic mouthpiece to be accommodated is described. Accordingly, in the packaging container for an orthodontic mouthpiece, when the label is adhered to the upper surface of the packaging container main body so as to seal, the orthodontic mouthpiece can be surrounded and housed by the plastic packaging container main body, specifically the accommodating portion and the lid portion of the accommodating portion main body, and it is possible to prevent the orthodontic mouthpiece from moving significantly within the accommodating portion by forming the accommodating portion so as to have a U-shaped transverse cross sectional shape. Therefore, the inventor has inquired into a matter that the orthodontic mouthpiece can be carried without being damaged.

Further, the accommodating container main body is constructed by an accommodating portion for accommodating the orthodontic mouthpiece, a first flange portion provided around the accommodating portion and forming as a flat shape which is the same as the shape of the lid portion in combination with the accommodating portion, and second flange portions positioned at right and left side ends of the first flange portion and respectively extended in an outward direction from an upper end of a step portion having the same height as a thickness of the lid portion. Accordingly, it is possible to position an upper surface of the lid portion constructing the upper surface of the packaging container main body and an upper surface of each of the second flange portions on a plane having the same height with no step at a time of closing the lid, and it is possible to seal by adhering the label to the upper surface. Therefore, the inventor has inquired into a matter that the label is not damaged even in the case that the upper surface of the packaging container for an orthodontic mouthpiece is pressed at a time of carrying. Further, since the upper surface of the lid portion and the upper surface of each of the second flange portions constructing the upper surface of the packaging container main body are positioned on the flat surface having the same height, the inventor has inquired into a matter that a cut line is formed in the label in such a manner as to be along a boundary line between the lid portion and each of the second flange portions, and it is possible to easily unseal only by cutting off the cut line.

Further, an engagement concave portion is formed in a front portion in the center of the first flange portion, and an engagement convex portion engaging with the engagement concave portion is formed at a position corresponding to the engagement concave portion of the first flange portion at a time of closing the lid portion. Accordingly, since the lid portion is not unnecessarily opened even after unsealing on the basis of the engagement between the engagement concave portion and the engagement convex portion, the packaging container can be used as a storage container for the orthodontic mouthpiece. Further, since the accommodated orthodontic mouthpiece is replaced by preparing a new orthodontic mouthpiece per a period of time from about two weeks to one month and sending it to a patient, the inventor has inquired into a matter that a sanitary state can be secured by using a new packaging container for an orthodontic mouthpiece in which a new orthodontic mouthpiece is accommodated, as a storage container which is exclusive for the orthodontic mouthpiece.

In other words, according to the present invention, there is provided a packaging container for an orthodontic mouthpiece constructed by a packaging container main body made of plastic being provided with an accommodating portion main body having an accommodating portion for accommodating an orthodontic mouthpiece having a U-shaped transverse cross sectional shape and a hinge portion in a rear end of the accommodating portion main body and a lid portion so as to be freely opened and closed via the hinge portion, and a label for sealing the packaging container main body made paper, resin, or cardboard on which a product information of an orthodontic mouthpiece to be accommodated is described, wherein the accommodating container main body is constructed by a first flange portion being provided around the accommodating portion and forming as a flat shape which is the same as the shape of the lid portion in combination with the accommodating portion, and second flange portions rising from right and left side ends of the first flange portion via step portions having the same height as a thickness of the lid portion and extended in an outward direction from an upper end of each of the step portions, wherein an engagement concave portion is formed in a front portion in the center of the first flange portion of the accommodating portion main body, and an engagement convex portion engaging with the engagement concave portion is formed at a position corresponding to the engagement concave portion of the first flange portion at a time of closing the lid portion, and wherein the label is adhered to an upper surface of the lid portion and an upper surface of each of the second flange portions constructing an upper surface of the packaging container main body so as to seal the packaging container main body, and the label is unsealed by cutting off a cut line formed in such a manner as to be along a boundary line between the lid portion and each of the second flange portions.

Further, the inventor has inquired into a matter that a grip portion protruding out of an end in an opposite side to the hinge portion side may be preferably formed in the lid portion. Accordingly, it is easy to carry out an unsealing work and an opening and closing work of the lid portion at a storing time.

Effect of the Invention

Since the packaging container for an orthodontic mouthpiece according to the present invention is constructed by the packaging container main body made of plastic and constituted by the accommodating portion main body having the accommodating portion for accommodating an orthodontic mouthpiece and the hinge portion in a rear ended the accommodating portion main body and the lid portion so as to be freely opened and closed via the hinge portion, and the label made of paper, resin, or cardboard being adhered to the upper surface of the packaging container main body so as to seal, and on which a product information of an orthodontic mouthpiece to be accommodated is described, it is possible to surround and house the orthodontic mouthpiece by the plastic packaging container main body, specifically the accommodating portion and the lid portion of the accommodating portion main body, when the label is adhered to the upper surface of the packaging container main body so as to seal. Further, since the accommodating portion is formed so as to have the U-shaped transverse cross sectional shape, the orthodontic mouthpiece does not move significantly within the accommodating portion. Therefore, it is possible to carry the orthodontic mouthpiece without damaging.

Further, since the accommodating container main body is constructed by the accommodating portion for accommodating the orthodontic mouthpiece, the first flange portion provided around the accommodating portion and forming as the flat shape which is the same as the shape of the lid portion in combination with the accommodating portion, and the second flange portions positioned at the right and left side ends of the first flange portion and respectively extended in the outward direction from the upper end of the step portion having the same height as the thickness of the lid portion, it is possible to position the upper surface of the lid portion constructing the upper surface of the packaging container main body and the upper surface of each of the second flange portions on the plane having the same height with no step at a time of closing the lid, and it is possible to seal by adhering the label to the upper surface. Therefore, the label is not damaged even in the case that the upper surface of the packaging container for an orthodontic mouthpiece is pressed at a time of carrying. Further, since the upper surface of the lid portion and the upper surface of each of the second flange portions constructing the upper surface of the packaging container main body are positioned on the flat surface having the same height, it is possible to easily unseal only by cutting off the cut line, by forming the cut line in the label in such a manner as to be along the boundary line between the lid portion and each of the second flange portions.

Further, since the engagement concave portion is formed in the front portion in the center of the first flange portion, and the engagement convex portion engaging with the engagement concave portion is formed at the position corresponding to the engagement concave portion of the first flange portion at a time of closing the lid portion, the lid portion is not unnecessarily opened on the basis of the engagement between the engagement concave portion and the engagement convex portion even after unsealing. Therefore, the packaging container can be used as the storage container for the orthodontic mouthpiece. Further, a sanitary state can be secured by using the packaging container for an orthodontic mouthpiece as an exclusive storage container for the orthodontic mouthpiece.

Further, in the case that the grip portion protruding out of the end in the opposite side to the hinge portion side is formed in the lid portion, it is easy to carry out the unsealing work and the opening and closing work of the lid portion at the storing time, so that the structure is preferable.

DESCRIPTION OF REFERENCE NUMERALS

Figure 1:
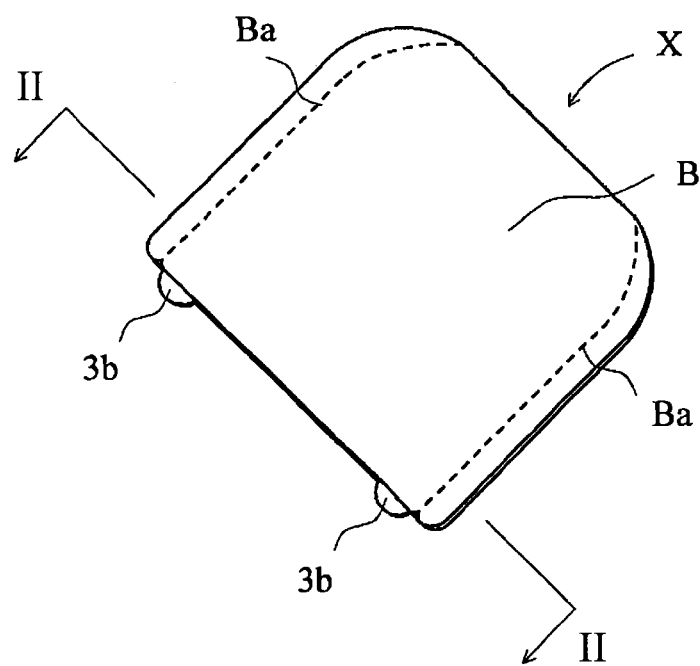
FIG. 1 is a perspective view illustrating an embodiment of a packaging container for an orthodontic mouthpiece according to the present invention.

X packaging container for orthodontic mouthpiece
A packaging container main body
1 accommodating portion main body
1a accommodating portion
1b first flange portion
1ba engagement concave portion
1c step portion
1d second flange portion
2 hinge portion
3 lid portion
3a engagement convex portion
3b grip portion
B label
Ba cut line
Y packaging bag for orthodontic mouthpiece
Ya sealing portion
Z packaging container for orthodontic mouthpiece according to prior art
Za packaging container main body
Zaa accommodating portion
Zb sealing seal

DETAILED DESCRIPTION OF PREFERRED EMBODIMENT

In the drawings, reference symbol X denotes a packaging container for an orthodontic mouthpiece according to the present invention. The packaging container for an orthodontic mouthpiece is constructed by a packaging container main body A coming to a base body, and a label B adhered to an upper surface of the packaging container main body A so as to seal.

Figure 3:
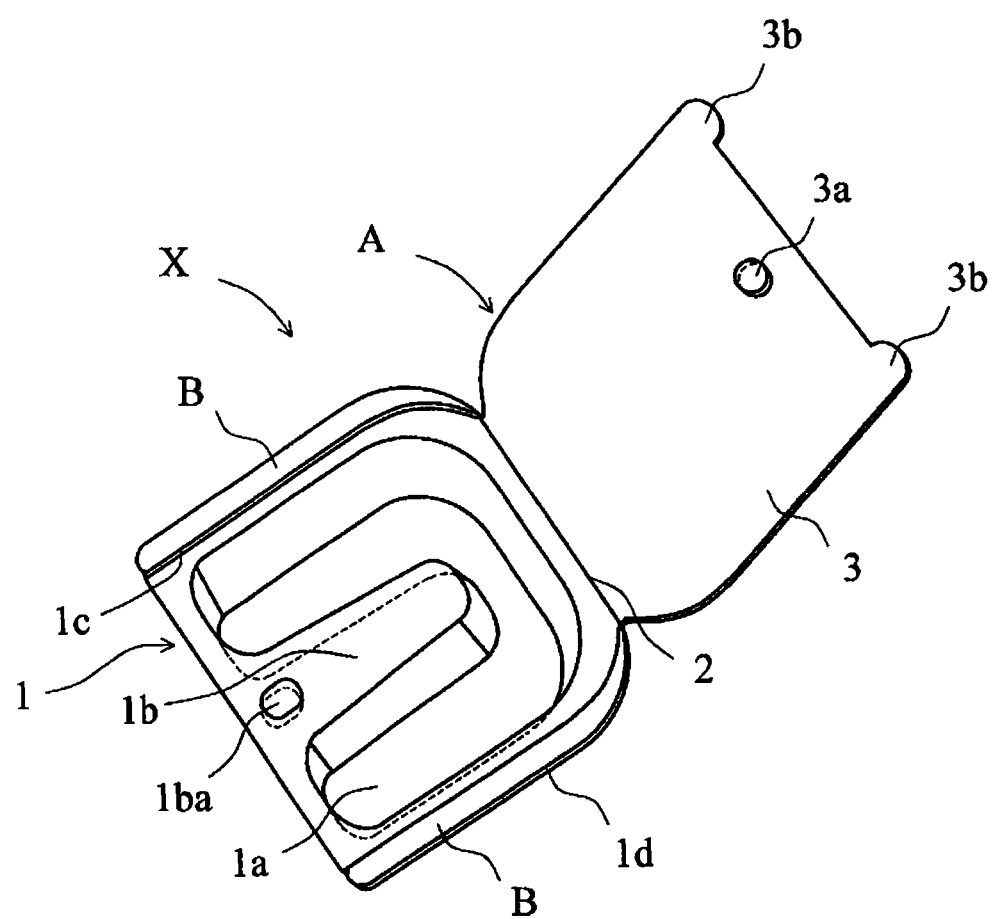
FIG. 3 is a perspective reference view illustrating a state in which the packaging container for an orthodontic mouthpiece is unsealed and a lid portion is opened.
Figure 4:
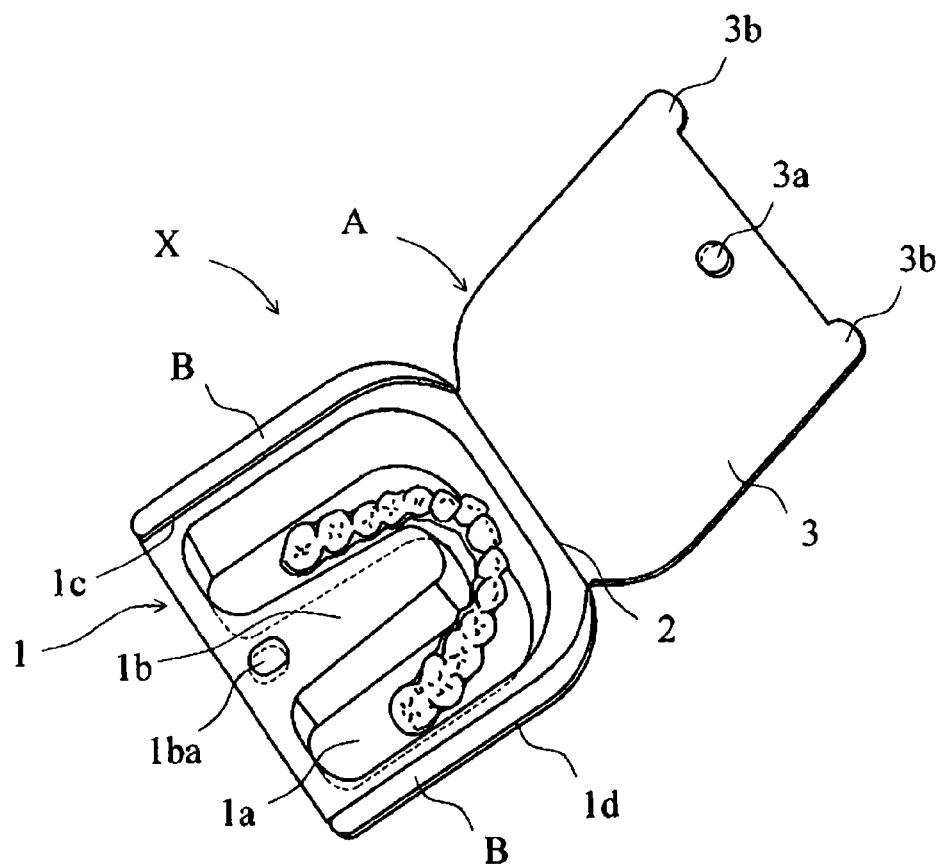
FIG. 4 is a perspective reference view illustrating a used state of the packaging container for an orthodontic mouthpiece in FIG. 3.

The packaging container main body A is constructed, as illustrated in FIGS. 3 and 4, by an accommodating portion main body 1 for accommodating an orthodontic mouthpiece, a hinge portion 2 in a rear end of the accommodating portion main body 1, and a lid portion 3 so as to be freely opened and closed via the hinge portion 2. The packaging container main body A is produced by injection molding or compression molding a plastic material, for example, polystyrene, polyethylene, polyethylene terephthalate (PET) or the like, and the accommodating portion main body 1, the hinge portion 2 and the lid portion 3 are integrally formed. Further, it is preferable that the packaging container main body A is constructed by a translucent raw material.

Figure 2:
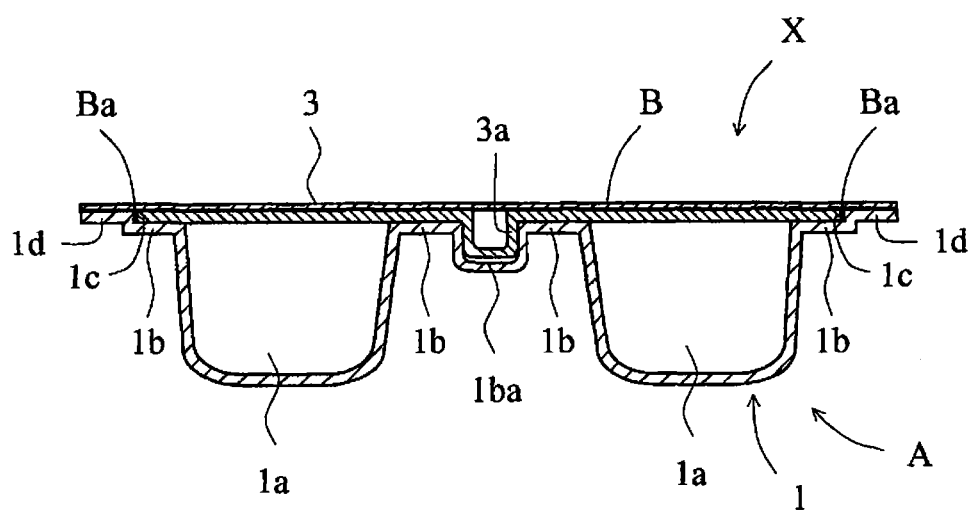
FIG. 2 is an enlarged cross sectional view along line II-II of FIG. 1.
Figure 5:
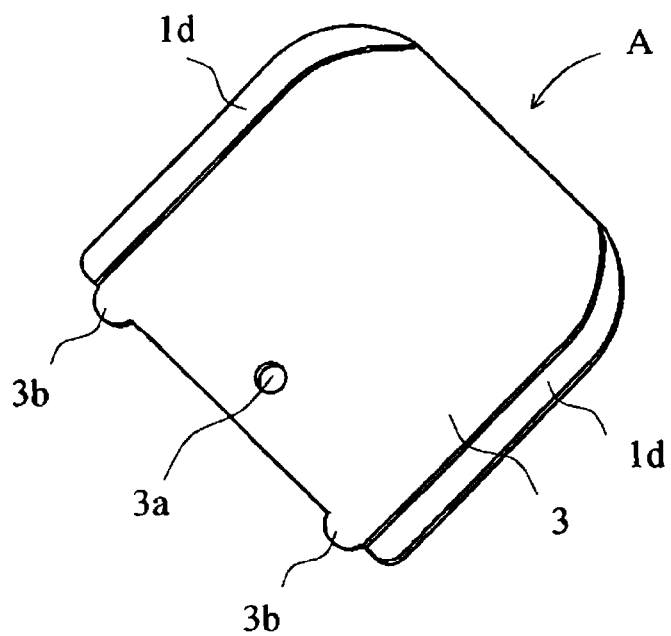
FIG. 5 is a perspective view illustrating an embodiment of a packaging container main body.
Figure 6:
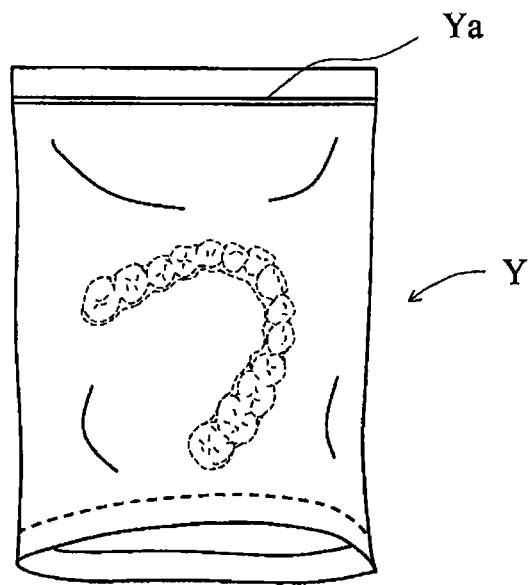
FIG. 6 is a perspective view illustrating an example of a packaging bag according to the prior art made of polyethylene or the like having a sealing portion in an upper opening.
Figure 7:
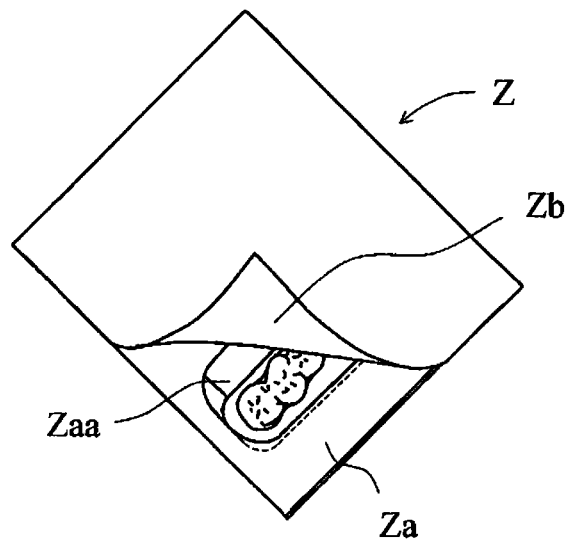
FIG. 7 is a perspective reference view illustrating a state in which a packaging container according to the prior art is partly unsealed, the packaging container being constructed by a plastic packaging container main body having an accommodating portion for accommodating an orthodontic mouthpiece, and a sealing seal for sealing the accommodating portion.

The accommodating portion main body 1 is constructed by an accommodating portion 1a for accommodating the orthodontic mouthpiece, a first flange portion 1b provided around the accommodating portion 1a, and second flange portions 1d and 1d respectively extended in an outward direction from upper ends of step portions 1c and 1c which are positioned in right and left side ends of the first flange portion 1b. Further, the accommodating portion 1a is formed so as to have a U-shaped transverse cross sectional shape. Further, as illustrated in FIGS. 2 and 5, a planar shape of a combination between an opening portion of the accommodating portion 1a and the first flange portion 1b is formed as the same shape as a planar shape of the lid portion 3, and is formed such that a height of each of the step portions 1c and 1c coincides with a thickness of the lid portion 3. Accordingly, an upper surface of the packaging container main body A is constructed by an upper surface of the lid portion 3 and an upper surface of each of the second flange portions 1d and 1d which are positioned on the plane having the same height with no step, at a time of closing the lid. Further, as illustrated in FIGS. 2, 3 and 4, an engagement concave portion 1ba is formed in a front portion in the center of the first flange portion 1b, the engagement concave portion 1ba engaging with an engagement convex portion 3a of the lid portion 3 mentioned below at a time of closing the lid.

A structure of the hinge portion 2 is not limited particularly as long as the hinge portion 2 can join the accommodating portion main body 1 and the lid portion 3 so as to freely carry out an opening and closing work of the lid portion 3. However, in the case that the hinge portion 2 is constructed by segmentized fine lines, the hinge portion is hard to be cut at a time of the opening and closing work, and can be disconnected at a time of disposing thereof. Accordingly, this structure is preferable.

The lid portion 3 is formed as the same planar shape as a planar shape of the combination of the opening portion of the accommodating portion 1a and the first flange portion 1b. Further, as illustrated in FIGS. 2, 3 and 4, the engagement convex portion 3a is formed at a position engaging with the engagement concave portion 1ba of the first flange portion 1b at a time of closing the lid. In addition, in the case that a grip portion 3b protruding out of an end in an opposite side to the hinge portion side is formed in the lid portion 3, it becomes easy to carry out an unsealing work and an opening and closing work of the lid at a time of storing. Accordingly, this structure is preferable. Further, it is further preferable to form the grip portions 3b and 3b in such a manner as to respectively protrude out of both right and left corners of an end in an opposite side to the hinge portion side of the lid portion 3, as illustrated in FIGS. 1, 3, 4 and 5.

The label B constructs the upper surface of the packaging container main body A, and is adhered to the upper surface of the lid portion 3 and the upper surface of each of the second flange portions 1d and 1d which are positioned on the flat surface having the same height with no step so as to seal the packaging container main body A. Further, as illustrated in FIGS. 1 and 2, cut lines Ba and Ba are formed in such a manner as to along a boundary line between the lid portion 3 and each of the second flange portions 1d and 1d. The label B is made of paper, resin or cardboard, and product information of the accommodated orthodontic mouthpiece such as a patient name, a period of use, an explanation and a product name is described on a front surface thereof. In this case, as a describing method of the information, for example, a method of directly printing on the label B can be thought, however, the method is not particularly limited as long as the method can display on the front surface of the label B. In the packaging container X for the orthodontic mouthpiece according to the present invention as mentioned above, since the label B made of paper, resin or cardboard on which a product information of an orthodontic mouthpiece to be accommodated is described is adhered to the upper surface of the packaging container main body A made of plastic and constituted by the accommodating portion main body 1 having the accommodating portion 1a for accommodating the orthodontic mouthpiece and the hinge portion 2 in a rear end of the accommodating portion main body 1 and a lid portion so as to be freely opened and closed via the hinge portion 2 so as to seal, it is possible to surround and house the orthodontic mouthpiece by the plastic packaging container main body A, specifically the accommodating portion 1a and the lid portion 3 of the accommodating portion main body 1. Further, since the accommodating portion 1a is formed so as to have the U-shaped transverse cross sectional shope, the accommodated orthodontic mouthpiece does not move significantly within the accommodating portion 1a. Therefore, it is possible to carry the orthodontic mouthpiece without damaging.

Further, since the planar shape of the combination of the opening portion of the accommodating portion 1a and the first flange portion 1b is formed as the same shape as the planar shape of the lid portion 3, it is possible to construct the upper surface of the packaging container main body A by the upper surface of the lid portion 3 and the upper surface of each of the second flange portions 1d and 1d at a time of closing the lid. Further, since it is formed such that the height of each of the step portions 1c and 1c coincides with the thickness of the lid portion 3, the upper surface of the lid portion 3 and the upper surface of each of the second flange portions 1d and 1d are positioned on the flat surface having the same height with no step. Therefore, the label B does not break even in the case of being pressed. Further, since the cut lines Ba and Ba are formed in the label B in such a manner as to be along the boundary line between the lid portion 3 and each of the second flange portions 1d and 1d, it is possible to easily unseal only by cutting off the cut lines Ba and Ba.

Further, since the engagement concave portion 1ba is formed in the front portion in the center of the first flange portion 1b, and the engagement convex portion 3a engaging with the engagement concave portion 1ba is formed at the position corresponding to the engagement concave portion 1ba of the first flange portion 1b at a time of closing the lid portion, the lid portion 3 is not unnecessarily opened on the basis of the engagement between the engagement concave portion 1ba and the engagement convex portion 3a even after unsealing. Therefore, the packaging container can be used as a storage container for the orthodontic mouthpiece. Further, a sanitary state can be secured by using the packaging container for an orthodontic mouthpiece as an exclusive storage container for the orthodontic mouthpiece.

Further, in the case that a grip portion 3b protruding out of the end in the opposite side to the hinge portion side is formed in the lid portion 3, it is easy to carry out the unsealing work and the opening and closing work of the lid portion at a time of storing, so that the structure is preferable.

What is claimed is:

1. A packaging container for an orthodontic mouthpiece comprising:
    a packaging container main body made of plastic being provided with an accommodating portion main body having an accommodating portion for accommodating an orthodontic mouthpiece having a U-shaped transverse cross sectional shape, and a hinge portion in a rear end of the accommodating portion main body, and a lid portion so as to be freely opened and closed via the hinge portion; and
    a label for sealing the packaging container main body made of paper, resin or cardboard on which a product information of an orthodontic mouthpiece to be accommodated is described,
    wherein the accommodating portion main body is constructed by a first flange portion being provided around the accommodating portion and forming as a flat shape which is the same as the shape of the lid portion in combination with the accommodating portion, and second flange portions rising from right and left side ends of the first flange portion via step portions having the same height as a thickness of the lid portion, and extended in an outward direction from an upper end of each of the step portions,
    wherein an engagement concave portion is formed in a front portion in the center of the first flange portion of the accommodating portion main body, and an engagement convex portion engaging with the engagement concave portion is formed at a position corresponding to the engagement concave portion of the first flange portion at a time of closing the lid portion, and
    wherein the label is adhered to an upper surface of the lid portion and an upper surface of each of the second flange portions constructing an upper surface of the packaging container main body so as to seal the packaging container main body, and the label is unsealed by cutting off a cut line formed in such a manner as to be along each of a boundary line between the lid portion and each of the second flange portions.

2. The packaging container for an orthodontic mouthpiece according to claim 1, wherein a grip portion protruding out of an end in an opposite side to the hinge portion side is formed in the lid portion.

* * * * *